(12) United States Patent
Dieterle et al.

(10) Patent No.: US 7,795,470 B2
(45) Date of Patent: Sep. 14, 2010

(54) METHOD FOR THE HETEROGENEOUSLY CATALYZED PARTIAL DIRECT OXIDATION OF N-PROPANE TO ACRYLIC ACID

(75) Inventors: Martin Dieterle, Jersey City, NJ (US); Joerg Heilek, Bammental (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 42 days.

(21) Appl. No.: 12/142,444

(22) Filed: Jun. 19, 2008

(65) Prior Publication Data

US 2008/0319224 A1 Dec. 25, 2008

Related U.S. Application Data

(60) Provisional application No. 60/945,393, filed on Jun. 21, 2007.

(30) Foreign Application Priority Data

Jun. 21, 2007 (DE) .................. 10 2007 029 053

(51) Int. Cl.
*C07C 51/16* (2006.01)
(52) U.S. Cl. .................................................. 562/549
(58) Field of Classification Search ................ 562/547, 562/549
See application file for complete search history.

(56) References Cited

U.S. PATENT DOCUMENTS

| | | | |
|---|---|---|---|
| 6,036,880 A | 3/2000 | Komada et al. | |
| 6,063,728 A | 5/2000 | Hinago et al. | |
| 6,143,916 A | 11/2000 | Hinago et al. | |
| 6,858,754 B2 | 2/2005 | Borgmeier et al. | |
| 7,005,403 B2 | 2/2006 | Borgmeier et al. | |
| 7,214,822 B2 | 5/2007 | Borgmeier et al. | |
| 7,238,827 B2 | 7/2007 | Hechler et al. | |
| 7,279,075 B2 | 10/2007 | Thiel et al. | |
| 7,326,802 B2 | 2/2008 | Hechler et al. | |
| 2004/0116741 A1 | 6/2004 | Nordhoff et al. | |
| 2004/0147393 A1 | 7/2004 | Hibst et al. | |
| 2004/0204607 A1 | 10/2004 | Machhammer et al. | |
| 2004/0229753 A1 | 11/2004 | Hibst et al. | |
| 2004/0245681 A1 | 12/2004 | Dieterle et al. | |
| 2005/0222459 A1 | 10/2005 | Nordhoff et al. | |
| 2005/0261511 A1 | 11/2005 | Fushimi et al. | |
| 2006/0258529 A1 | 11/2006 | Diefenbacher et al. | |
| 2007/0149807 A1 | 6/2007 | Dieterle et al. | |
| 2007/0149808 A1 | 6/2007 | Dieterle et al. | |

FOREIGN PATENT DOCUMENTS

| | | |
|---|---|---|
| DE | 24 13 463 | 10/1975 |
| DE | 198 35 247 A1 | 2/1999 |
| DE | 100 51 419 A1 | 4/2002 |
| DE | 101 22 027 A1 | 5/2002 |
| DE | 102 45 585 A1 | 4/2004 |
| DE | 102 54 279 A1 | 6/2004 |
| DE | 103 60 057 A1 | 7/2004 |
| DE | 103 59 027 A1 | 5/2005 |
| EP | 0 529 853 A2 | 3/1993 |
| EP | 0 603 836 A1 | 6/1994 |
| EP | 0 608 838 A2 | 8/1994 |
| EP | 0 895 809 A1 | 2/1999 |
| EP | 1 090 684 A1 | 4/2001 |
| EP | 1 192 987 A1 | 4/2002 |
| EP | 1 254 707 A1 | 11/2002 |
| EP | 1 254 709 A2 | 11/2002 |
| WO | WO 02/32571 A1 | 4/2002 |
| WO | WO 02/055469 A1 | 7/2002 |
| WO | WO 03/078378 A1 | 9/2003 |
| WO | WO 2004/031106 A1 | 4/2004 |
| WO | WO 2004/063138 A1 | 7/2004 |
| WO | WO 2004/089856 A2 | 10/2004 |
| WO | WO2004089856 * | 10/2004 |
| WO | WO 2004/099081 A1 | 11/2004 |
| WO | WO 2006/120233 A1 | 11/2006 |
| WO | WO 2007/074044 A1 | 7/2007 |
| WO | WO 2007/074045 A1 | 7/2007 |

* cited by examiner

*Primary Examiner*—Taylor Victor Oh
(74) *Attorney, Agent, or Firm*—Oblon, Spivak, McClelland, Maier & Neustadt, L.L.P.

(57) ABSTRACT

A method for the heterogeneously catalyzed partial direct oxidation of propane to acrylic acid in the gas phase, in which the reaction gas inlet mixture comprises cyclopropane as an impurity and the acrylic acid, after it has been converted from the product gas mixture into the liquid phase, is operated from the other constituents of the liquid phase with the aid of a separation by crystallization.

7 Claims, No Drawings

METHOD FOR THE HETEROGENEOUSLY CATALYZED PARTIAL DIRECT OXIDATION OF N-PROPANE TO ACRYLIC ACID

DESCRIPTION

The present invention relates to a method for the heterogeneously catalyzed partial direct oxidation of n-propane to acrylic acid, in which a reaction gas inlet mixture comprising n-propane, molecular oxygen and at least one inert diluent gas is fed to a reaction stage, the n-propane present in the reaction gas inlet mixture is directly oxidized to acrylic acid in the reaction stage by passing the reaction gas inlet mixture at elevated temperature through a catalyst bed comprising a catalyst present in the solid state of aggregation, the conversion of n-propane during a single pass through the catalyst bed being $\geq 10$ mol % and the selectivity $S^{AA}$ of the acrylic acid formation, based on converted n-propane, being $\geq 40$ mol %, the reaction gas mixture is then fed, as product gas mixture comprising acrylic acid, out of the reaction stage into a first separation zone, acrylic acid present in the product gas mixture of the reaction stage is converted into the liquid phase in the first separation zone and remaining as a residual product gas mixture comprising n-propane and depleted in acrylic acid is removed from the first separation zone and at least a portion of the n-propane present in the residual product gas mixture is recycled to the reaction stage and acrylic acid is separated from the liquid phase in a second separation zone by using at least one thermal separation method.

Acrylic acid is an important intermediate which is used as such or in the form of its alkyl esters for the production of, for example, polymers suitable as adhesives or polymers which are superabsorbents for water (cf. for example WO 02/055469 and WO 03/078378).

Their preparation by heterogeneously catalyzed partial direct oxidation of n-propane in one reaction stage is known (cf. for example DE-A 102 45 585, WO 2004/031106, WO 2006/120233, US 2005/0261511, DE-A 103 60 057, DE-A 103 59 027, WO 2004/099081, WO 02/32571, WO 2004/089856, EP-A 529 853, EP-A 603 836, EP-A 608 838, EP-A 895 809, DE-A 198 35 247, DE-A 100 51419, DE-A 101 22 027, EP-A 1 254 707, EP-A 1 254 709, EP-A 1 192 987, EP-A 1 090 684, DE-A 102 54 279 and the literature cited in these publications).

The term direct oxidation means that in each case the formation of acrylic acid occurs directly over the catalysts used in the reaction stage on passage of the reaction gas mixture comprising n-propane through the catalyst bed. That is to say, the catalyst bed is not of a nature such that, when the reaction gas mixture comprising n-propane flows through the catalyst bed, initially mainly intermediates which can be isolated, such as, for example, propylene and acrolein, are formed in the first longitudinal sections thereof in the direction of flow, from which the acrylic acid would form only in the further longitudinal sections of the catalyst bed which are downstream in the direction of flow. Rather, at least individual catalysts concomitantly used in the catalyst bed are capable in each case of catalyzing all the various reaction steps to be covered on the reaction route from n-propane to acrylic acid, so that acrylic acid formation from n-propane can take place or takes place over each of the catalysts having its capability.

The n-propane required as starting substance for this procedure (frequently referred to in this document only as a "propane" for reasons of simplicity) is usually added to the reaction gas inlet mixture as crude propane (also referred to as "crude propane" in this document). In contrast to chemically pure propane, crude propane also comprises constituents which differ chemically from propane and they may account for up to 10% by volume and more, based on the crude propane (cf. for example WO 2006/120233). In principle, it is possible to separate all impurities present in crude propane from propane present therein (cf. for example DE-A 24 13 463). However, this is not required when the impurities are inert in heterogeneously catalyzed partial oxidation of the propane to acrylic acid. If the latter property is present, impurities in the reaction gas inlet mixture act simply as inert diluent gases.

In this document, inert diluent gases are understood as meaning very generally those gases which, in the course of partial oxidation, each remain chemically unchanged to an extent of at least 95 mol %, preferably at least 97 mol % and particularly preferably at least 99 mol % or more. In the conversion of the acrylic acid from the product gas mixture into the liquid phase, these inert gases usually remain as residual gas in the gas phase and, after the partial oxidation, can therefore be separated from the acrylic acid as the target product in a comparatively simpler manner than would be the case in the separation from the propane prior to the partial oxidation.

WO 2006/120233 discloses that $C_4$-hydrocarbons can act as catalyst poisons in a heterogeneously catalyzed partial direct oxidation of propane to acrylic acid, and it is for this reason that it is expedient in terms of application technology substantially to separate $C_4$-hydrocarbons from crude propane before the crude propane is used as raw material for the acrylic acid preparation. Usually, the hydrocarbon contents of the crude propane which have five or more carbon atoms are also separated at $C_4$-hydrocarbons from the propane present in said crude propane. The corresponding prior separation of $C_2$-hydrocarbon impurities from crude propane is considered to be unnecessary in WO 2006/120233.

Separating off the other $C_3$-hydrocarbons (cyclopropane, propylene) differing from propane and frequently also present in crude propane is considered to be unnecessary in WO 2006/120233. This is firstly because the relevant catalysts usually also partially oxidize propylene to acrylic acid and the cyclopropane content in crude propane is usually a low one. However, WO 2006/120233 states nothing about the fate of cyclopropane as a constituent of the reaction gas mixture of a heterogeneously catalyzed partial direct oxidation of propane.

According to the teaching of US 2005/0261511, the purity of crude propane used for a heterogeneously catalyzed partial direct oxidation of propane is substantially unimportant.

At the same time, US 2005/0261511 considers the presence of $CO_2$ and $H_2O$ in the reaction gas inlet mixture of a heterogeneously catalyzed partial direct oxidation of propane to be advantageous in terms of an acrylic acid yield which is as high as possible.

The prior applications PCT/EP2006/069526 and PCT/EP2006/069527 relate to the presence of cyclopropane in the reaction gas mixture of an heterogeneously catalyzed partial gas-phase oxidation of propylene to acrylic acid.

The oxidizing agent molecular oxygen can be added to the reaction gas inlet mixture of a heterogeneously catalyzed partial direct oxidation of propane both in pure form and as a mixture with gases substantially inert with respect to the partial direct oxidation (e.g. $N_2$ in air). Air is the preferred oxygen source. Inert diluent gases, such as $N_2$, $H_2O$, CO, $CO_2$, He and/or Ar, etc., absorb the heat of reaction and keep the reaction gas mixture outside the explosion range.

As a rule, multielement oxides present in the solid state of aggregation are used as catalysts for heterogeneously catalyzed partial direct oxidation of propane to acrylic acid. The reaction stage can be carried out over the multielement oxides present in the solid stage of aggregation, in a fixed catalyst bed, fluidized catalyst bed or moving catalyst bed (fluid catalyst bed).

The conversion of the acrylic acid present in the product gas mixture of a heterogeneously catalyzed partial direct propane oxidation into the liquid phase can be effected by absorption and/or condensation, according to the teaching of WO 2004/089856. According to the teaching of WO 2004/089856, the acrylic acid can be separated from the liquid phase subsequently with the use of at least one thermal separation method.

Thermal separation methods are to be understood as meaning (as also in this document) those methods in which at least two material phases different from one another (e.g. liquid/liquid; gaseous/liquid; solid/liquid; gaseous/solid, etc.) are produced and are brought into contact with one another. Owing to the physical and temperature gradients existing between the phases, heat exchange and mass transfer takes place between them, the latter being caused by the desired separation (isolation). The term thermal separation methods reflects the fact that it requires either the withdrawal or the supply of heat in order to produce the formation of the material phases and/or that withdrawal or the supply of thermal energy promotes or maintains the mass transfer.

Thermal separation methods in the context of the present invention are therefore distillations, rectifications, crystallizations, extractions, azeotropic distillations, azeotropic rectifications, stripping, desorption, etc. (cf. also WO 04/063138).

Thermal separation methods involving crystallization are considered to be entail particularly high capital costs and as a rule attempts are therefore made to avoid them.

In the course of our own work it was surprisingly found that cyclopropane, a not infrequent impurity constituent in crude propane, is partially oxidized in the course of a heterogeneously catalyzed partial direct oxidation of propane to acrylic acid, as described at the outset, not like propylene, which is structurally isomeric with cyclopropane, and also not like n-propane, also substantially to acrylic acid. It is true that cyclopropane isomerizes on heating to 100 to 200° C. in the presence of catalysts (e.g. Pt) to propylene (cf. for example Lehrbuch der Organischen Chemie, Beyer•Walter, Hirzel Verlag Stuttgart, page 390, 1991). In the course of a heterogeneously catalyzed partial direct oxidation of propane to acrylic acid, however, it behaves completely differently from propylene and does not react like the latter likewise to give virtually exclusively acrylic acid but in a completely unexpected manner to give propionic acid to a large and surprisingly considerable extent and is mainly responsible for the byproduct formation thereof during a heterogeneously catalyzed partial direct oxidation of propane. It was an undesired impurity in acrylic acid simply because of its unpleasant odor even in small amounts and owing to its incapability of undergoing free radical polymerization.

The object of the present invention was therefore to use this surprising accidental finding in an advantageous manner in the context of the preparation of acrylic acid having as low a content of propionic acid as possible via the route of a heterogeneously catalyzed partial direct oxidation of propane to acrylic acid. It was also intended to do this against the background, that the abovementioned isomerization to propylene could be a suitable route for eliminating the cyclopropane before the partial oxidation. In principle, propylene and cyclopropane can also be separated from one another by rectification since their boiling points at atmospheric pressure (1 bar) are sufficiently different from one another (b.p. of propylene=−47° C.; b.p. of cyclopropane=−32.8° C.). The abovementioned problem and its reservation are of particular interest especially because, in a method according to the preamble, at least a portion of the n-propane present in the residual product gas mixture is recycled to the reaction stage in this step. Such recycling will usually be accompanied by recycling of cyclopropane and completely converted in the partial oxidation, resulting in an increasing concentration of cyclopropane in the partial oxidation reaction stage.

For achieving the object according to the invention, it has now been found that it is expedient, at least up to cyclopropane contents of 1% by volume in the reaction gas inlet mixture (based on propane present in reaction gas inlet mixture), to leave the cyclopropane as an impurity in the crude propane and to separate the propionic acid formed therefrom in the partial oxidation from the target product of acrylic acid by ensuring that the at least one thermal separation method in the second separation zone comprises at least one isolation of acrylic acid by crystallization (as a result of comparable condensation points (at 1 bar, acrylic acid: 141° C., propionic acid: 141.35° C.), the propionic acid is usually converted together (i.e. as an accompanying substance with acrylic acid) with acrylic acid into the liquid phase in the first separation zone).

Accordingly, the present application provides a method for the heterogeneously catalyzed partial direct oxidation of propane to acrylic acid, in which a reaction gas inlet the mixture comprising a propane, molecular oxygen and at least one inert diluent gas is fed to a reaction stage, the propane present in the reaction gas inlet mixture is directly partially oxidized to acrylic acid in the reaction stage by passing the reaction gas inlet mixture at elevated temperature through a catalyst bed comprising a catalyst present in the solid state of aggregation, the conversion of propane during a single pass through the catalyst bed being $\geq 10$ mol % and the selectivity $S^{AA}$ of the acrylic acid formation, based on converted propane, being $\geq 40$ mol %, the reaction gas mixture is then fed, as product gas mixture comprising acrylic acid, out of the reaction stage into a first separation zone (separation zone 1), acrylic acid present in the product gas mixture of the reaction stage is converted into the liquid phase in the first separation zone and remaining gaseous residual product gas mixture comprising n-propane and depleted in acrylic acid is removed from the first separation zone (separation zone 1) and at least a portion of the n-propane present in the residual product gas mixture is recycled to the reaction stage and acrylic acid is separated from the liquid phase in a second separation zone (separation zone 2) by using at least one thermal separation method, wherein the reaction gas inlet mixture comprises, based on its total volume, from 2 to 50% by volume of propane,
from 0.1 to 60% by volume of $CO_2$,
from 1 to 50% by volume of $O_2$,
from 1 to 50% by volume of $H_2O$ and,
based on the molar amount of propane present in the reaction gas inlet mixture,
from >0 up to 1 mol % of cyclopropane and the at least one thermal separation method in the second separation zone comprises at least one isolation of acrylic acid by crystallization.

Isolation of acrylic acid by crystallization is understood as meaning that the acrylic acid accumulates in the crystals formed and the secondary components accumulate in the remaining mother liquor. The determination of the cyclopropane content (and of the other contents) can be effected, for example, by gas chromatography.

The method according to the invention is therefore particularly suitable even when the reaction gas inlet mixture, based on the molar amount of propane (n-propane) present therein, comprises from 10 molppb to 1 mol % or from 50 molppb to 0.9 mol % or from 100 molppb to 0.8 mol % or from 1 molppm to 7000 molppm or from 10 molppm to 5000 molppm or from 100 molppm to 4000 molppm or from 200 molppm to 3000 molppm or from 300 molppm to 2000 molppm or 400 molppm or 500 molppm to 1500 molppm or from 750 to 1250 molppm of cyclopropane.

However, the method according to the invention is also suitable when the reaction gas inlet mixture, based on the molar amount of propane (n-propane) present therein, comprises from 10 molppb to 1000 molppm or from 50 molppb to 800 molppm or from 100 molppb to 600 molppm or from 1 molppm to 500 molppm or from 10 molppm to 400 molppm or from 50 molppm to 300 molppm or from 100 to 200 molppm of cyclopropane.

The conversion of the acrylic acid present in the product gas mixture of the partial direct oxidation according to the invention into the liquid phase can be carried out in separation zone 1 of the method according to the invention in principle in a manner known from the methods of the prior art (cf. for example WO 2004/089856).

They are substantially characterized in that the acrylic acid is converted from the gaseous into the liquid phase by measures comprising absorption and/or condensation.

As a rule, the product gas mixture resulting in the reaction stage in the method according to the invention is first subjected to indirect and/or direct cooling on entry into separation zone 1.

The cooled (typically to 150 to 250° C.) or uncooled product gas mixture of the partial direct oxidation can be fed, for example in an absorption column, countercurrent to liquid absorbent which ascends in the absorption column and absorbs the acrylic acid from the product gas mixture, as mentioned in corresponding cases, for example in JP-A 2001/0026269, in EP-A 990 636, in JP-A 2000/327651, in EP-A 925 272, in EP-A 695 736, in EP-A 778 255, in DE-A 21 36 396, in DE-A 24 49 780, in DE-A 43 08 087, in EP-A 982 287, in EP-A 982 289, in EP-A 982 288 and in DE-A 196 31 645.

Suitable absorbents are both water, aqueous solutions (e.g. aqueous sodium hydroxide solution or aqueous acrylic acid) and/or organic solvents (e.g. alcohols used for the esterification of acrylic acid, such as, for example, 2-ethylhexanol, and higher boiling (preferably hydrophobic) organic solvents). According to the invention, the boiling point of the organic solvent is preferably at least 20° C., in particular at least 50° C. and particularly preferably at least 70° C. above the boiling point (based on a pressure of 1 bar) of acrylic acid. Organic absorbents prepared according to the invention have boiling points (at 1 bar) of from 180 to 400° C., in particular from 220 to 360° C. Absorbents which are very particularly suitable according to the invention are high-boiling, extremely hydrophobic solvents which comprise no externally acting polar group, such as aliphatic or aromatic hydrocarbons, e.g. middle oil fractions from paraffin distillation, or ethers having bulky groups on the O atom, or mixtures thereof, and a polar solvent, such as 1,2-dimethyl phthalate disclosed in DE-A 43 08 087, can advantageously be added thereto. Furthermore, esters of benzoic acid and phthalic acid with straight-chain alkanols comprising 1 to 8 carbon atoms are suitable, such as n-butyl benzoate, methyl benzoate, ethyl benzoate, dimethyl phthalate, diethyl phthalate, and so-called heat transfer oils, such as biphenyl, diphenyl ether and mixtures of biphenyl and diphenyl ether or the chlorine derivatives thereof and triarylalkanes, e.g. 4-methyl-4'-benzyldiphenylmethane and isomers thereof, such as 2-methyl-2'-benzyldiphenylmethane, and mixtures of such isomers.

An absorbent which is very particularly preferred for acrylic acid is a solvent comprising biphenyl and diphenyl ether, preferably in the azeotropic composition, in particular comprising about 25% by weight of biphenyl and about 75% by weight of diphenyl ether, based on 100% by weight of biphenyl and diphenyl ether, for example the commercially available Diphyl®. The solvent mixture furthermore preferably comprises a polar solvent, such as dimethyl phthalate, in an amount of from 0.1 to 25% by weight, based on the total solvent mixture. When a high-boiling organic solvent is used as the absorbent, the product gas mixture is advantageously cooled prior to the absorption by partial evaporation of the absorbent in a direct condenser or quench apparatus. Venturi scrubbers, bubble columns or spray condensers are particularly suitable for this purpose.

In this document, the terms high, medium and low boiler mean compounds which have a higher boiling point than acrylic acid at atmospheric pressure (1 bar) (high boilers), about the same boiling point as acrylic acid (medium boilers) and a lower boiling than acrylic acid (low boilers), respectively.

Very generally, the countercurrent absorption is advantageously carried out in a column comprising internals having separation effects. For example, structured packings, random packings and/or trays (e.g. dual-flow trays and/or valve trays or bubble trays) are suitable as such internals having a separation effect. As a rule, the absorbent (e.g. the organic solvent) comes into contact with it from above. The product gas mixture (and, if appropriate, vaporized absorbent from the quench apparatus) is usually passed into the absorption column from below and then cooled to the absorption temperature in a manner expediently used. The cooling is advantageously effected by cooling circulations. In other words, heated absorbent descending in the column is taken up from the absorption column, cooled in heat exchangers and recycled to the absorption column at a point above the take-off point. After the absorption, substantially all high boilers, a major part of the acrylic acid and of the medium boilers (e.g. the propionic acid formed from the cyclopropane) and a part of the low boilers are present in the absorbent.

The unabsorbed residual product gas mixture remaining gaseous during the absorption can be further cooled in order to separate off the easily condensable part of the low-boiling second components (e.g. water, formaldehyde and acetic acid) (as a rule referred to as dilute acid solution). According to the teaching of WO 2004/089856, the remaining residual product gas mixture comprising unconverted propane can, for example, be divided into two portions of identical composition and one of the two portions can be recycled as recycle gas into the reaction stage (expediently as a constituent of the reaction gas inlet mixture) and the other portion can be discharged. According to the invention, preferably no separation of dilute acid solution takes place.

Particularly since steam is concomitantly used as diluent gas in the reaction stage of the method according to the invention (with the use of multielement oxide active materials (e.g. multimetal oxide active materials) as catalytically active materials, this is advantageous for the selectivity of the acrylic acid formation), the conversion according to the invention of acrylic acid present in the product gas mixture of the reaction stage into the liquid phase (independently of which conversion method, particularly among the conversion methods described in this document, is used) is preferably effected in such a way that the molar ratio W of the steam present in the remaining residual product gas mixture to the propane present therein is not more than 50%, better not more than 40 or 30%, even better not more than 20 or 10%, preferably not more than 5%, less than the corresponding molar ratio W* in the product gas mixture of the reaction stage (based on W*). In the extreme case, the abovementioned ratios W and W* may also be identical. The purpose of the attempt to leave as much steam as possible in the residual product gas mixture is to be able and as substantially as possible to dispense with a fresh supply (a condensation and revaporization) of steam to the reaction gas inlet mixture in the case of an above-described division of the residual product gas mixture into two portions of identical composition and discharge of one portion and recycling the other portion as recycled gas to the reaction stage. However, that portion of the residual product gas mixture which is discharged must comprise at least the same amount of water as is formed as byproduct in the reaction stage, in order to prevent an increase in the concentration of water in the reaction gas mixture (the more selectively the heterogeneously catalyzed partial gas-phase oxidation was carried out in the reaction stage the smaller is the amount of water to be discharged). In the discharge procedure described, this also applies in a corresponding manner to other secondary components in a reaction stage. If air is used as an oxygen source in the method according to the invention, the amount of residual product gas mixture discharged will simultaneously be such that the amount of nitrogen present therein corresponds at least to that amount present in the air supply.

If one of the high-boiling organic solvents is used as the absorbent, the absorption in the above case is preferably carried out so that the outflow from the absorption column is a single phase. Besides, the steam content in the residual product gas mixture remaining in gaseous form in the absorption can be adjusted by a suitable choice in the absorption temperature, independently of the absorbent chosen.

Alternatively to the conversion of the acrylic acid into a liquid phase by absorption in a solvent (absorbent), this conversion can also be effected by condensation, in particular fractional condensation, as described, for example, in DE-A 199 24 532, DE-A 102 00 583, DE-A 100 53 086, DE-A 196 27 847, DE-A 197 40 253, DE-A 197 40 252, DE-A 197 40 253, DE-A 198 14 387 and DE-A 102 47 240.

The product gas mixture of the reaction stage is subjected to a fractional condensation, ascending into itself, in a separation column provided with internals having a separation effect, if appropriate after direct and/or indirect cooling, and the acrylic acid is removed as a constituent of a liquid side take-off in the separation column.

Tray columns which comprise, from bottom to top, first dual-flow trays and thereafter hydraulically sealed cross-flow trays as internals having a separation effect, as described in the abovementioned prior art are preferred as the condensation column comprising internals having a separation effect.

According to the invention, the abovementioned fractional condensation is also advantageously and expediently carried out in such a way that substantially no separation of water present in the product gas mixture takes place. In other words, heretoo, preferably no separation of dilute acid solution takes place.

However, a portion of the residual product gas mixture which is discharged and has the composition of the residual product gas mixture can also be washed with water prior to its discharge, in order to avoid acrylic acid losses. The acrylic acid can be extracted from the resulting acrylic acid-containing dilute acid solution, for example with the organic absorbent used for the absorption, and can be combined with the absorbate.

Very generally, the polymerization inhibition is effected in the course of the conversion of acrylic acid from the product gas mixture into a liquid phase as described in the prior art by addition of corresponding polymerization inhibitors.

Of course, the recycling according to the invention of propane present in the residual product gas mixture in the reaction stage can also be effected so that the propane present in the residual product gas mixture (usually including propylene and cyclopropane present in the residual product gas mixture) is separated from residual product gas mixture before this recycling.

This separation can be effected, for example, by absorption of the propane (and, if appropriate, propylene and/or cyclopropane) in an organic solvent, such as tetradecane. By subsequent desorption and/or stripping with, for example, air (which can simultaneously act as an oxygen source in the reaction stage), the absorbed propane (and, if appropriate, propylene and/or cyclopropane) can be liberated again and recycled to the reaction stage (cf. for example DE-A 102 45 585). In principle, separation of the propane from the residual product gas mixture before its recycling to the reaction stage can, however, also be carried out, for example, by fractional rectification under pressure. It is expedient in terms of application technology if the total amount of propane present in the residual product gas mixture is recycled to the reaction stage.

The further separation of the acrylic acid from the liquid phase in which it is present can now be carried out in the method according to the invention according to the procedure used in separation zone 1 and according to the method conditions chosen specifically for the partial direct oxidation of the propane to acrylic acid and hence determining the remaining secondary component spectrum (reaction temperature, inert diluent gases chosen, catalysts chosen, content and molar ratio of the reactants in the reaction gas inlet mixture, etc.) by different combinations of a very wide range of thermal separation methods to the desired (arbitrary) purity of the acrylic acid. These may be, for example, combinations of methods comprising extraction, desorption, rectification, azeotropic distillation, azeotropic rectification, distillation and/or stripping.

All that is important according to the invention is that the combination of the thermal separation methods used altogether for further separation of the acrylic acid in separation zone 2 comprises at least one separation of acrylic acid by crystallization. This requirement is due to the fact that a greater depletion of propionic acid is associated with a separation of acrylic acid by crystallization, whereas such great depletion cannot be achieved by other thermal separation methods. In other words, crystals which are enriched in acrylic acid are deposited in the method according to the invention by cooling from at least one liquid phase comprising acrylic acid and obtained in at least one thermal separation method to be used in separation zone 2. Usually, the crystals comprise substantially exclusively acrylic acid.

In principle, at least one separation of acrylic acid by crystallization can be effected in the method according to the invention directly from an acrylic acid-containing liquid phase obtained in the conversion of the acrylic acid from the product gas mixture into the liquid phase.

For example, according to the teaching of DE-A 198 38 845, the separation by crystallization can be effected directly from the absorbate comprising absorbed acrylic acid (under certain circumstances, said absorbate can be subjected beforehand to stripping and/or desorption in order to separate off volatile constituents for the crystallization from the absorbate substantially more easily than acrylic acid; such more readily volatile constituents may be, for example, acetic acid, formic acid and/or lower aldehydes. If appropriate, absorbent can also be removed by distillation before the separation by crystallization, in order thus to increase the content of acrylic acid in the absorbate and consequently to ensure that acrylic acid forms the crystalline phase separating out on cooling (or the resulting crystalline phase enriched with acrylic acid). The abovementioned is true both when the absorbate comprises acrylic acid and an organic solvent has a higher boiling point than acrylic acid (cf. for example DE-A 198 38 845; possible absorbents are, for example, biphenyl, diphenyl ether, mixtures of the two abovementioned agents and mixtures of biphenyl, diphenyl ether and dimethyl phthalate) and when water or an aqueous solution was used as the absorbent (cf. for example WO 02/055469 and WO 03/078378). As a rule, the crystals obtained in the separation by crystallization are additionally washed as a further separation or purification measure. Suitable washing agents are, for example, pure absorbent and/or acrylic acid prepared beforehand and already having the desired purity. In principle, washing can also be effected by sweating. The crystals are heated and the more highly contaminated crystals melting at a lower temperature become liquid and throw away the impurities as wash liquid. However, the crystallization can also be effected directly from condensate obtained in a fractional condensation (preferably removed via a side take-off) and enriched with acrylic acid, as described, for example, in WO 04/035514. In principle, the washing of the crystals deposited can also be carried out in a wash column (this may be a static, a hydraulic or a mechanical wash column, as described, for example, in WO 01/77056).

In principle, the crystallization treatment to be used according to the invention of at least one liquid phase P comprising acrylic acid in separation zone 2 is not subject to any limitation, including the method for separating the mother liquor from the crystals (all methods stated in the prior art mentioned in this document can be used). In other words, it can be carried out in one stage or a plurality of stages, continuously or batchwise. In particular, it can also be carried out as a fractional crystallization. Usually in a fractional crystallization, all stages which produce acrylic acid crystals which are purer than the liquid phase P fed in are referred to as purification stages and all other stages as stripping stages. Expediently, multistage methods are operated according to the countercurrent principle in which, after the crystallization in each stage, the crystals are separated from the mother liquor and these crystals are fed to the respective stage with the next highest purity while the crystallization residue is fed to the respective stage with the next lowest purity.

Frequently, the temperature of the liquid phase P during the deposition of the crystals enriched with acrylic acid is from −25° C. to +14° C., in particular from 12° C. to −5° C.

For example, the separation of the acrylic acid by crystallization from the liquid phase P containing such acrylic acid, if separation is required according to the invention, can be carried out as layer crystallization (cf. DE-A 26 06 364, EP-A 616 998, EP-A 648 520 and EP-A 776 875). Here, the crystals are frozen in the form of cohesive, firmly adhering layers. The separation of the deposited crystals from the remaining residual melt (also referred to as mother liquor) is effected in the simplest case by simple flowing away of the residual melt. In principle, a distinction is made between "static" and "dynamic" layer crystallization methods. Forced convection of the liquid phase P is characteristic of the dynamic layer crystallization of liquid phases P comprising acrylic acid. Said convection can be effected by circulation of the liquid phase P through pipes with a full flow cross section by pumping, by feeding the liquid phase P as a trickle film (e.g. according to EP-A 616 998) or by passing inert gas into a liquid phase P or by pulsation.

In the static method, the liquid phase P is stationary (e.g. in tube-bundle or plate-pipe heat exchangers) and is deposited in the form of layers by slow temperature cooling on the secondary side. Thereafter, the residual melt (mother liquor) is discharged, more highly contaminated fractions are sweated out of the crystal layer by slow temperature increase and the pure product is then melted (cf. WO 01/77056).

Frequently, the combination of dynamic and static layer crystallization is used for at least one separation of the acrylic acid by crystallization in separation zone 2 (cf. EP-A 616 998).

According to the invention, the at least one separation of the acrylic acid by crystallization from the liquid phase P (in particular from all liquid phases P mentioned by way of example in this document) is preferably carried out, however, according to the teaching of WO 01/77056, WO 02/055469 and WO 03/078378 as a suspension crystallization.

As a rule, the crystal suspension comprising suspended acrylic acid crystals is produced by cooling the liquid phase P, the acrylic acid crystals having a lower propionic acid content and the residual melt (mother liquor) having a higher propionic acid content (relative to the respective total amount) than the liquid phase P.

The acrylic acid crystal can grow directly in suspension and/or can be deposited as a layer on a cooled wall, from which they are subsequently scrapped off and resuspended in the residual melt (mother liquor).

All suspension crystals and suspension crystallization methods mentioned in WO 01/77056, WO 02/055469 and WO 03/078378 are suitable according to the invention. As a rule, the acrylic acid crystal suspension produced thereby has a solids content of from 20 to 40% by weight.

Furthermore, all methods mentioned in the abovementioned WO publications are intended for the separation of suspension crystals formed and remaining mother liquor are suitable (e.g. mechanical separation methods, such as centrifugation). According to the invention, the separation is preferably effected in a wash column (for example a gravimetric, hydraulic or mechanical one; cf. WO 01/77056). This is preferably a wash column having forced transport of the deposited acrylic acid crystals. The crystal volume fraction in the crystal bed reaches as a rule values of >0.5. As a rule, the wash column is operated at values of from 0.6 to 0.75. The wash liquid used is advantageously the melt of acrylic acid crystals purified (separated off) beforehand in the wash column. The washing is usually effected by the countercurrent method. The method according to the invention thus comprises in particular methods which comprise the following method steps:

a) crystallization of acrylic acid out of a liquid phase P,
b) separation of the acrylic acid crystals from the remaining mother liquor (residual melt, liquid residual phase),
c) at least partial melting of the acrylic acid crystals separated off and
d) at least partial recycling of the molten acrylic acid crystals to step b) and/or to step a).

Step b) is preferably effected by countercurrent washing with molten acrylic acid crystals separated off beforehand and recycled to step b).

According to the invention, the liquid phase P advantageously comprises water for the use of the acrylic acid separation by crystallization according to the invention, since, according to the teaching of WO 01/77056 and WO 03/078378, formation of acrylic acid crystals in the presence of water results in a particularly advantageous crystal form for the subsequent separation of the crystals from the remaining mother liquor for the product according to the invention. This is true in particular when the crystallization is carried out as a suspension crystallization and even more so if the subsequent separation of mother liquor is carried out in a wash column, and even more so if the melt of acrylic acid crystals already purified in the wash column is used as wash liquid.

In other words, the separation of acrylic acid by crystallization which is required according to the invention comprises in particular methods in which the liquid phase P comprising acrylic acid is converted under the action of cooling into a crystal suspension consisting of acrylic acid crystals and liquid residual phase (residual melt), the proportion by weight of propionic acid in the acrylic acid crystals being smaller and the proportion by weight of propionic acid in the liquid residual phase (the mother liquor) being greater than the proportion by weight of propionic acid in the liquid phase P, if appropriate a part of the remaining mother liquor is separated mechanically from the crystal suspension and the acrylic acid crystals are freed from the remaining mother liquor in a wash column, with the proviso that
a) the liquid phase P, based on the acrylic acid present therein, comprises from 0.20 to 30, frequently up to 20, often up to 10, % by weight of water and
b) the melt of acrylic acid crystals purified in the wash column is used as wash liquid.

In particular, the method according to the invention comprises the above methods, the liquid phase P having $\geq 80\%$ by weight of acrylic acid or $\geq 90\%$ by weight of acrylic acid or $\geq 95\%$ by weight of acrylic acid.

Furthermore, it is advantageous according to the invention if the water content of the liquid phase P in procedures described above (or very generally for the use of the method according to the invention) is 0.2 or 0.4 to 8 or up to 10 or up to 20 or up to 30% by weight or from 0.6 to 5% by weight or from 0.60 to 3% by weight, based acrylic acid present in the liquid phase P.

All of the abovementioned is true in particular when the wash column is a wash column having forced transport of the acrylic acid crystals, and this especially when it is a hydraulic or a mechanical wash column according to WO 01/77056 and its operated as mentioned there.

All of the abovementioned is true especially when the wash column is designed and is operated according to the teachings of WO 03/041832 and WO 03/041833.

According to the invention, the at least one separation of acrylic acid by crystallization does not necessarily have to be effected directly from the liquid phase obtained in separation zone 1 and comprising the acrylic acid in condensed form. Rather, the liquid phase obtained in separation zone 1 and comprising the acrylic acid is first subjected to a thermal separation method or a combination of thermal separation methods, in the course of which the acrylic acid-containing liquid phase P to be crystallized according to the invention is obtained.

Often, the acrylic acid-containing liquid phase P to be crystallized according to the invention is therefore the result of an application of at least one thermal separation method differing from crystallization (e.g. distillation, rectification, extraction, distraction, desorption, stripping, azeotropic rectification, adsorption and/or azeotropic distillation) to the acrylic acid-containing liquid phase obtained in separation zone 1 and/or to subsequent phases resulting in the course of the application (cf. for example DE-A 196 06 877). Frequently, the abovementioned methods are used many times for producing the acrylic acid-containing liquid phase P to be treated by crystallization. For example, the acrylic acid-containing liquid phase P to be crystallized according to the invention may be a crude acrylic acid obtained analogously to DE-A 103 36 386 from the absorbate of the product gas mixture of a propylene partial oxidation by using various thermal separation methods differing from a crystallization, said absorbate being obtained in separation zone 1. Such a crude acrylic acid to be crystallized according to the invention can, however, also be obtained from an aqueous absorbate obtained in separation zone 1 of the method according to the invention, analogous to the teachings of EP-A 695 736, EP-A 778 255 or EP-A 1 041 062 with the concomitant use of at least one azeotropic distillation.

In the method according to the invention, the propionic acid discharge may be present in principle exclusively in the at least one acrylic acid separation by crystallization. In this case, the discharge will consist of mother liquor enriched with propionic acid.

If the separation by crystallization to be used according to the invention is carried out, for example, by means of a combination of dynamic and static crystallization according to EP-A 616 998, the mother liquor discharge enriched with propionic acid will expediently be present in the region of the static crystallization.

According to the invention, in a method according to the invention, the sharp separation method of the at least one acrylic acid separation by crystallization in the second separation zone is advantageously coupled back to at least one unsharp separation method in the first (preferably) and/or second separation zone so that the mother liquor remaining in the acrylic acid separation by crystallization is recycled at least partly to at least one of the unsharp separation methods.

The basic structure of such a coupled application of unsharp separation methods and the sharp separation method of the crystallization is taught, for example, by DE-A 196 06 877, EP-A 792 867 and EP-A 1 484 308, EP-A 1 484 309, EP-A 1 116 709 and in particular EP-A 1 015 410.

An unsharp separation method is defined as a separation method in which the composition of the phase forming during use of the separation method and enriched with acrylic acid is dependent in a pronounced manner on the composition of the mixture to be separated, whereas the separation by crystallization which is required according to the invention is a sharp separation method in that the composition of the acrylic acid crystals forming is substantially independent (ideally there is complete independence) of the composition of the acrylic acid-containing liquid phase P. An absorption and/or a fractional condensation used in separation zone 1 for converting acrylic acid from the product gas mixture into the condensed phase are likewise unsharp separation methods, such as, for example, an extraction and/or rectification in separation zone 2.

In the case of such a coupling of a sharp separation method in separation zone 2 and an unsharp separation method in, for example, separation zone 1, the method according to the invention is of considerable importance in that, in continuous operation of such a procedure, the propionic acid increases in concentration in the acrylic acid-containing liquid phase P to be treated according to the invention by crystallization, via the recycling of mother liquor, since the mother liquor is enriched with propionic acid.

A coupling of unsharp and sharp separation to be used as described in the method according to the invention expediently also has a discharge (this may be the only discharge of the method) for at least one material stream enriched with propionic acid beyond the mother liquor. For example, it is possible to use as such a discharge the bottom liquid of a separation column (for example of the absorption or condensation column in separation zone 1), from which the liquid phase P itself or the material stream to be converted in the further course into the liquid phase P is taken up, for example, via a side take-up and/or top take-off.

Alternatively, however, a separate propionic acid discharge stream can also be taken off at a point in the separation column (for example that present in separation zone 1) at which the propionic acid bulge is present (in addition to the discharge for the liquid phase P) and from this to enrich the propionic acid in the mother liquor in a second separation preferably comprising fractional crystallization (e.g. combination of dynamic and static crystallization according to EP-A 616 998) and to discharge such a mother liquor (preferably from the static crystallization). Molten material from the purified crystal fraction can be recycled to the separation column and/or introduced into the crystallization of the acrylic acid-containing liquid phase P. In principle, such a propionic acid discharge stream can also be a part-stream taken from the liquid phase P.

Of course, all method steps carried out in separation zones 1, 2 (as already discussed) are carried out with inhibition of polymerization. It is possible to proceed thereby as described in the prior art mentioned. An outstanding position among all the available acrylic acid method stabilizers is occupied by dibenzo-1,4-thiazine (PTZ), 4-hydroxy-2,2,6,6-tetramethylpiperidin-1-oxyl (4-OH-TEMPO) and p-methoxyphenol (MEHQ). They may be, for example either each by themselves or in pairs or as a ternary mixture, the constituent of the acrylic acid-containing liquid phase P to be treated according to the invention by crystallization. Usually, the total amount of polymerization inhibitors present in the liquid phase P is from 0.001 to 2% by weight, based on the acrylic acid present therein.

Overall, the method according to the invention permits the preparation of acrylic acid having superabsorbent suitability (such acrylic acid can of course also be used for all other uses discussed in WO 02/055469 and WO 03/078378), in spite of the content of cyclopropane in the reaction gas inlet mixture, by the sequence comprising heterogeneous catalyzed partial direct oxidation of the propane present in the reaction gas inlet mixture to acrylic acid, fractional acrylic acid condensation from the product gas mixture of the partial oxidation, suspension crystallization of the acrylic acid condensate taken off and separation of the suspension crystals from the remaining mother liquor in a wash column with the use of a pure crystal melt as wash liquid, in an efficient manner and with the use of only one crystallization stage.

Besides, the heterogeneously catalyzed partial direct oxidation of the propane to acrylic acid can be carried out with the use of a reaction gas inlet mixture to be used according to the invention, by the method disclosed in the prior art for the heterogeneously catalyzed partial direct oxidation of propane to acrylic acid (it is possible here in particular to adopt a procedure as described in the publications EP-A 1 335 793, US 2005/0261511, WO 2004/089856 and the prior art cited in these publications).

Suitable catalysts for the method according to the invention are in principle all those which are recommended in the prior art for the heterogeneously catalyzed partial direct oxidation of propane to acrylic acid.

According to US 2005/0261511, these are in particular those catalysts of which the active material consists of at least one multielement oxide of the general stoichiometry 0

$$J_j M_m N_n Y_y Z_z O_o \quad (0),$$

where
J=Mo and/or W,
M=V and/or Ce,
N=Te, Sb and/or Se,
Y=at least one element from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu,
Z=Ni, Pd, Cu, Ag and/or Au,
j=1,
m=from 0.01 to 1,
n=from 0.01 to 1,
y=from 0.01 to 1,
z=from 0.001 to 1 and
o=a number which is determined by the valency and frequency of the elements other than oxygen in (0), or comprises at least one such multielement oxide.

The multielement oxide active materials suitable according to the invention include in particular the multimetal oxide active materials of the publications EP-A 608 838, JP-A 3-170445, EP-A 609 122, EP-A 747 349, EP-A 529 853, DE-A 102 54 279, DE-A 198 35 247, EP-A 895 809, JP-A 7-232071, JP-A 11-169716, DE-A 102 61 186, EP-A 1 192 987, JP-A 10-57813, JP-A 2000-37623, JP-A 10-36311, WO 00/29105, EP-A 767 164, DE-A 100 29 338, JP-A 8-57319, JP-A 10-28862, JP-A 11-43314, JP-A 11-574719, WO 00/29106, JP-A 10-330343, JP-A 11-285637, JP-A 310539, JP-A 11-42434, JP-A 11-343261, JP-A 3423262, WO 99/03825, JP-A 7-53448, JP-2000-51693, JP-A 11-263745, DE-A 100 46 672, DE-A 101 18 814, DE-A 101 19 933, JP-A 2000/143244, EP-A 318 295, EP-A 603836, DE-A 19832033, DE-A 19836359, EP-A 962 253, DE-A 101 19 933, DE-A 100 51 419, DE-A 100 46 672, DE-A 100 33 121, DE-A 101 459 58, DE-A 101 22 027, EP-A 1 193 240 and the literature cited in these publications.

These are substantially multimetal oxide active materials which comprise the elements Mo, V, at least one of the two elements Te and Sb, and at least one of the elements from the group consisting of Nb, Ta, W, Ti, Al, Zr, Cr, Mn, Ga, Fe, Ru, Co, Cs, Ca, Sr, Ba, Rh, Ni, Pd, Pt, La, Pb, Cu, Re, Ir, Y, Pr, Nd, Tb, Bi, B, Ce, Sn, Zn, Si, Na, Li, K, Mg, Ag, Au and In in combination.

The combination preferably comprises the elements Nb, Ta, W and/or Ti and particularly the element Nb from the last group of elements.

The relevant multimetal oxide active materials preferably comprise the abovementioned element combination in the stoichiometry I $$Mo_1 V_b M^1_c M^2_d \quad (I),$$

where
$M^1$=Te and/or Sb,
$M^2$=at least one of the elements from the group consisting of Nb, Ta, W, Ti, Al, Zr, Cs, Ca, Sr, Ba, Cr, Mn, Ga, Fe, Ru, Co, Rh, Ni, Pd, Pt, La, Bi, Pb, Cu, Re, Ir, V, Pr, Nd, Tb, Ce, Sn, Zn, Si, Na, Li, K, Mg, Ag, Au and In,
b=from 0.01 to 1,
c=from >0 to 1 and
d=from >0 to 1.

According to the invention, $M^1$ is preferably Te and $M^2$ is preferably Nb, Ta, W and/or Ti. $M^2$ is preferably Nb.

The stoichiometric coefficient b is advantageously from 0.1 to 0.6. In a corresponding manner, the preferred range for the stoichiometric coefficient c is from 0.01 to 1 or from 0.05 to 0.4, and advantageously values for d are from 0.001 to 1 or from 0.01 to 0.6.

According to the invention, it is particularly advantageous if the stoichiometric coefficients b, c and d are simultaneously in the abovementioned preferred ranges.

The abovementioned is true in particular when the active material of the catalyst load consists of an abovementioned element combination with respect to its elements differing from oxygen.

These are in particular the multimetal oxide active materials of the general stoichiometry II $$Mo_1V_bM^1_cM^2_dO_n \qquad (II),$$

the variables having the meaning mentioned with regard to stoichiometry I and n being a number which is determined by the valency and frequency of the elements other than oxygen in (II).

The relevant multimetal oxide materials preferably comprise the element combination mentioned at the outset in the stoichiometry III $$Mo_1V_{a'}M^4_{b'}M^5_{c'}M^6_{d'} \qquad (III)$$

where
$M^4$=at least one of the elements from the group consisting of Te and Sb;
$M^5$=at least one of the elements from the group consisting of Nb, Ti, W, Ta and Ce;
$M^6$=at least one of the elements from the group consisting of Pb, Ni, Co, Bi, Pd, Cs, Ca, Sr, Ba, Ag, Pt, Cu, Au, Ga, Zn, Sn, In, Re, Ir, Sm, Sc, Y, Pr, Nd and Tb;
a'=from 0.01 to 1;
b'=from >0 to 1;
c'=from >0 to 1; and
d'=from 0 to 0.5.
a' is preferably from 0.05 to 0.6, particularly preferably from 0.1 to 0.6 or 0.5.
b' is preferably from 0.01 to 1, particularly preferably from 0.01 or 0.1 to 0.5 or 0.4.
c' is preferably from 0.01 to 1, particularly preferably from 0.01 or 0.1 to 0.5 or 0.4.
d' is preferably from 0.00005 or 0.0005 to 0.5, particularly preferably from 0.001 to 0.5, frequently from 0.002 to 0.3 and often from 0.005 or 0.01 to 0.1.
$M^4$ is preferably Te.
$M^5$ preferably comprises 50 mol %, preferably at least 75 mol % and very particularly preferably at least 100 mol % of Nb, based on its total amount.
$M^6$ is preferably at least one element from the group consisting of Ni, Co, Bi, Pd, Ag, Au, Pb and Ga, particularly preferably at least one element from the group consisting of Ni, Co, Pd and Bi.

Very particularly preferably, $M^5$ comprises at least 50 mol % or at least 75 mol % or 100 mol % of Nb, based on its total amount, and $M^6$ is at least one element from the group consisting of Ni, Co, Pd and Bi.

In an outstanding manner according to the invention, $M^4$ is Te, $M^5$ is Nb and $M^6$ is at least one element from the group consisting of Ni, Co and Pd.

The abovementioned is true in particular when the active material of the catalyst load consists of an element combination of stoichiometry (III) with regard to elements differing from oxygen. These are in particular the multimetal oxide active materials for the general stoichiometry (IV)

$$Mo_1V_{a'}M^4_{b'}M^5_{c'}M^6_{d'}O_{n'} \qquad (IV),$$

the variables having the meaning mentioned with regard to stoichiometry III and n' being a number which is determined by the valency and frequency of the elements other than oxygen in (IV).

Furthermore, those multimetal oxide active materials which firstly comprise either one of the abovementioned element combinations (I), (III) or, with regard to the elements differing from oxygen, consist of them and in each case simultaneously have a X-ray diffraction pattern which shows reflections h and i whose peaks are at the diffraction angles (2Θ) 22.2±0.5° (h) and 27.3±0.5° (i) (all data relating in this document to an X-ray diffraction pattern are based on a X-ray diffraction pattern produced using CuKα radiation as X-rays (Siemens diffractometer theta-theta D-5000, tube voltage: 40 kV, tube current: 40 mA, aperture V20 (variable), collimator V20 (variable), secondary rmonochromator aperture (0.1 mm), detector aperture (0.6 mm), measuring interval (2Θ): 0.02°, measuring time per step: 2.4 s, detector: scintillation counter).

The half-width of these reflections can be very small or very pronounced.

Those of the abovementioned multimetal oxide active materials whose X-ray diffraction pattern has a reflection k whose peak is at 28.2±0.5° (k) in addition to the reflections h and i, are advantageous for the method according to the invention.

Preferred according to the invention along the latter in turn are those in which the reflection h has the strongest intensity within the X-ray diffraction pattern and has a half-width of at most 0.5°, and very particularly preferably those in which the half-width of the reflection i and of the reflection k is simultaneously in each case ≦1° and the intensity $P_k$ of the reflection k and the intensity $P_i$ of the reflection i prefer the relationship 0.2≦R≦0.85, better 0.3≦R≦0.85, preferably 0.4≦R≦0.85, particularly preferably 0.65≦R≦0.85, even more preferably 0.67≦R≦0.75 and very particularly preferably R=0.70 to 0.75 or R=0.72, in which R is the intensity ratio defined by the formula $$R=P_i/(P_i+P_k).$$

The abovementioned X-ray diffraction patterns preferably have no reflection whose maximum is at 2Θ=50±0.3°.

The definition of the intensity of a reflection in the X-ray diffraction pattern is based in this document on the definition recorded in DE-A 198 35 247, DE-A 101 22 027 and in DE-A 100 51 419 and DE-A 100 46 672. The same applies to the definition of the half-width.

In addition to the reflections h, i and k, the abovementioned X-ray diffraction pattern of such multimetal oxide active materials advantageously to be used according to the invention also comprise further reflections whose peaks are at the following diffraction angles (2Θ):
9.0±0.4° (l),
6.7±0.4° (o) and
7.9±0.4° (p).

It is furthermore advantageous if the X-ray diffraction pattern additionally comprises a reflection whose peak is at the diffraction angle (2Θ)=45.2±0.4° (q).

Frequently, the X-ray diffraction pattern also comprises the reflections 29.2±0.4° (m) and 35.4±0.4° (n).

It is furthermore advantageous if the element combinations defined in the formulae (I), (II), (III) and (IV) are present as pure i-phase. If the catalytically active oxide material also comprises a k-phase its X-ray diffraction pattern also comprises, in addition to the abovementioned reflections, further reflections whose peaks are at the following diffraction angles (2Θ): 36.2±0.4° and 50±0.4° (the terms i- and k-phase are used in this document as defined in DE-A 101 22 027 and DE-A 101 19 933).

If the reflection h is assigned the intensity 100, it is advantageous according to the invention if reflections i, l, m, n, o, p and q have the following intensities on the same intensity scale:

| | |
|---|---|
| i: | from 5 to 95, frequently from 5 to 80, in some cases from 10 to 60; |
| l: | from 1 to 30; |
| m: | from 1 to 40; |
| n: | from 1 to 40; |
| O: | from 1 to 30; |
| p: | from 1 to 30 and |
| q: | from 5 to 60. |

If the X-ray diffraction pattern comprises the abovementioned additional reflections, the half-width thereof is as a rule $\leq 10$.

The specific surface area of multimetal oxide active materials of the general formula (II) or (IV) which are to be used according to the invention or of multimetal oxide active materials which comprise the element combinations of the general formula (I) or (III) is often from 1 to 40 m$^2$/g or from 10 to 30 m$^2$/g (BET surface area, nitrogen), especially when the X-ray diffraction pattern is as described.

The preparation of the multimetal oxide active materials described is related to this prior art cited. This includes in particular US 2005/0261511, DE-A 103 03 526, DE-A 102 61 186, DE-A 102 54 279, DE-A 102 54 278, DE-A 101 22 027, DE-A 101 19 933, DE-A 100 33 121, EP-A 1192 987, DE-A 100 29 338, JP-A 2000-143244, EP-A 962 253, EP-A 895 809, DE-A 198 35 247, WO 00/29105, WO 00/29106, EP-A 529 853 and EP-A 608 838 (in all working examples of the two last-mentioned publications, spray-drying is to be used as a drying method; e.g. with an entrance temperature of from 300 to 350° C. and an exit temperature of from 100 to 150 C; countercurrent or cocurrent).

The multimetal oxide active materials described can be used as such (i.e. in powder form) or can be shaped into suitable geometries (for example like the coated catalyst of DE-A 100 51 419 or of the geometrical variants of DE-A 101 22 027) for the method according to the invention.

For carrying out the method according to the invention, all catalysts mentioned can be used in the catalyst bed both in undiluted form and in a form diluted with inert particles and/or moldings (they have no active material). A suitable diluent material is, for example, steatite.

The geometry of the diluent moldings is preferably identical to that of the catalyst moldings.

As described in the publications on multimetal oxide active material catalysts suitable for the method according to the invention and already mentioned in this document, the method according to the invention can be carried out both on fixed-bed catalyst loads and on fluidized-bed or fluid-bed catalyst loads.

The reaction temperatures, in particular with the use of the catalysts recommended in this document, may be from 200 to 700° C., preferably from 200 to 550° C. or from 230 to 480° C. or from 300 to 440° C.

The loading of the catalyst bed with propane may be from 50 to 10 000 or up to 30 000 I (S.T.P.)/I (catalyst load)/h, or from 80 to 1500 I (S.T.P.)/I/h or from 100 to 1000 I (S.T.P.)/I/h or from 120 to 600 I (S.T.P.)/I/h or from 140 to 300 I (S.T.P.)/I/h.

The loading of the catalyst load with reaction gas inlet mixture may be from 100 to 30 000 or up to 10 000 I (S.T.P.)/I/h or from 300 to 6000 I (S.T.P.)/I/h or from 300 to 2000 I (S.T.P.)/I/h. The average resonance time in the catalyst load may be from 0.01 to 10 s or from 0.1 to 10 s or from 2 to 6 s.

The operating pressure in the reaction stage can in principle be both below atmospheric pressure (=1 bar) and above 1 bar (cf. for example DE-A 198 35 247, EP-A 895 809 and DE-A 102 61 186). As a rule, the operating pressure is above atmospheric pressure for overcoming the pure resistances in the reaction stage. It is advantageous for the method according to the invention if the reaction gas inlet mixture is fed into the reaction stage at an inlet pressure such that the residual product gas mixture is also removed at an operating pressure of $\geq 1.5$ bar from separation zone 1. It is expedient in terms of application technology if the outer pressure of the residual product gas mixture on removal from separation zone 1 is as a rule not more than 30 or 25 bar, frequently not more than 20 bar. According to the invention, the abovementioned outer pressure is advantageously $\geq 1.5$ bar and $\leq 10$ bar, preferably $\geq 2$ bar and $\leq 8$ bar, frequently $\geq 3$ bar and $\leq 6$ bar or $\geq 5$ bar. Typically, the pressure at the entrance into the reaction stage is from 0.5 or 1 to 4 bar, in general from 1.5 to 3.5 bar, often from 2 to 3 bar, above the abovementioned outlet pressure. When the method according to the invention is carried out in the range of particularly high pressures, the pressure at the entrance into the reaction stage is as a rule less than 0.5 bar above the abovementioned outlet pressure. Typical pressures at the entrance into the reaction stage are therefore from 2.5 to 25 bar, as a rule from 3 to 10 bar and expediently according to the invention from 4 to 8 bar. Typical pressures at the entrance into separation zone 1 are from 3 to 25 bar, frequently from 3 to 20 bar or from 3 to 15 bar or from 3 to 8 bar.

The reaction gas inlet mixture preferably comprises, based on its total volume, from 5 to 60% by volume of $CO_2$.

Reaction gas inlet mixtures particularly preferred according to the invention comprise
 from 7 to 25% by volume of propane,
 from 10 to 50% by volume of $CO_2$,
 from 5 to 25% by volume of $O_2$,
 from 5 to 25% by volume of $H_2O$ and
 based on the molar amount of propane (n-propane) present in the reaction gas inlet mixture,
 up to 1 mol % of cyclopropane.

If, in the method according to the invention, the residual product gas mixture is divided into two portions of identical composition, and one portion A is discharged and the other portion B is recycled as recycle gas to the reaction stage, the ratio V as (portion B:portion A) is as a rule $\geq 0.5$ or $\geq 1$, in general $\geq 1.5$, preferably $\geq 2$ and particularly preferably $\geq 3$. Of course, in the method according to the invention V may be also be $\geq 8$ or $\geq 10$.

In a method according to the invention, V is usually $\leq 30$, in general $\leq 25$, frequently $\leq 20$. V is often $\leq 15$ or $\leq 10$, preferably from 2 to 8.

Other reaction gas inlet mixture compositions suitable according to the invention are those of WO 2004/089856, with the precondition that the $CO_2$ and cyclopropane contents required according to the invention are present in addition to the contents stated in WO 2004/089856.

The term "reaction stage" is used in this document in particular in the context of WO 2004/089856. In other words, in this document, it represents in particular one or more apparatuses which are connected in series and, apart from entrance and exit for the reaction gas inlet mixture and the product gas mixture and, if appropriate, further entrances for auxiliary gases, are closed on the gas side so that the pressure loss which gas mixture experiences on passing through such an apparatus or through such a series of apparatuses is limited to overcoming the flow resistances.

For example, the reaction stage may be a tube-bundle reactor, a fluidized-bed reactor, a fluid-bed reactor or a series of such reactors. However, a reactor as described above can of course comprise the possibility of introducing, for example, catalyst activator into the reactor whilst carrying out the method according to the invention, as described, for example, in WO 02/081421. In principle, it should also be possible to add inert gas and/or oxygen (e.g. air) between the reactors in a series of reactors. For example, in the heterogeneously catalyzed partial direct oxidation according to the invention of propane can be carried out in one-zone tube-bundle reactors, as described in EP-A 700 714 and in EP-A 700 893. However, it can also be carried out in multizone tube-bundle reactors, as described in DE-A 199 27 624, DE-A 199 48 242, DE-A 199 48 241, DE-A 199 10 508 and DE-A 199 10 506. A procedure in a fluidized bed can be carried out, for example, as described in WO 02/0811421.

Based on the propane present in the reaction gas inlet mixture, the conversion of propane in the method according to the invention is as a rule from 10 or 20 to 70 mol %, frequently from 30 to 60 mol % and often from 40 to 60 mol % or from 45 to 55 mol % based on a single pass of the reaction gas mixture through the reaction stage. The $S^{AA}$ of the acrylic acid formation is usually from 40 to 98 or up to 95 or up to 90 mol %, frequently from 50 to 80 mol %, often from 60 to 80 mol %, based on the propane converted in the reaction stage.

If separation zone 2 does not comprise any separation of acrylic acid by crystallization, advantageous procedures are those in which the reaction gas inlet mixture for the heterogeneously catalyzed partial direct oxidation of propane has as low a cyclopropane content as possible, preferably a vanishing cyclopropane content. A reduction in the cyclopropane content of the crude propane can be carried out, for example, in the same way as the reduction in the cyclopropane content of crude propylene as described in PCT/EP2006/069527.

EXAMPLES

I. Heterogeneously Catalyzed Partial Direct Oxidation of Propane

A tubular reactor produced from steel (internal diameter: 8.5 mm, length: 1.40 m, wall thickness: 2.5 cm) was loaded with 35.0 g of the spherical coated catalyst from the example of EP-A 1 335 793, whose active material of the composition $Mo_{1.0}V_{0.33}Te_{0.15}Nb_{0.11}O_x$ (catalyst bed length=55 cm). A preliminary bed of 30 cm of quartz chips (grain size: 1-2 mm) was installed before the catalyst bed, and a subsequent bed of the same quartz chips after the catalyst bed over the remaining length of the tubular reactor.

By means of electrically heated heating mats, the external temperature of the reaction tube thus loaded was set to 350° C. over the total length from the outside.

The reaction tube was then loaded with a reaction gas inlet mixture having the molar composition 3.3% by volume of n-propane, 10% by volume of molecular oxygen, 41.7% by volume of $H_2O$, 5.0% by volume of $CO_2$, X% by volume of cyclopropane and, as residual amount, $N_2$, (the entrance side was on the side of the subsequent bed).The reaction gas inlet mixture was preheated to 200° C. The residence time (based on the active material bed) was adjusted to 2.4 sec. The inlet pressure was 2 bar absolute.

The propane conversion was 27 mol %, based on the single pass of the reaction gas mixture through the fixed catalyst bed. The selectivity $S^{AA}$ was 60 mol %.

The acrylic acid formed was condensed out of the product gas mixture by direct cooling with condensate formed beforehand, cooled to 4° C. and provided with hydroquinone polymerization inhibitor.

The table below shows the increase Y in the amount of propionic acid present in the condensate, stated in ppm by weight and based on the amount of acrylic acid present in the condensate, associated with increasing cyclopropane content X* (stated here, however, in mol % relatively to the molar amount of propane present in the reaction gas inlet mixture) in the reaction gas inlet mixture.

TABLE

| X* (mol %) | Y (ppm by weight) |
|---|---|
| 0.05 | 0.036 |
| 0.8 | 0.58 |

II. Separation from Acrylic Acid-Containing Liquid Phase P by Crystallization

The liquid phase P had the following contents:

95.201% by weight of acrylic acid, 0.042% by weight of methacrylic acid, 0.604% by weight of benzaldehyde, 0.062% by weight of propionic acid, 0.687% by weight of furan-2-aldehyde, 0.663% by weight of acetic acid, 0.004% by weight of furan-3-aldehyde, 0.002% by weight of allyl acrylate, 0.009% by weight of acrolein and 2.20% by weight of water.

It was subjected to polymerization inhibition by addition of 150 ppm by weight of monomethyl ether of hydroquinone (MEHQ) and <1000 ppm by weight of phenotziazine (based on acrylic acid present).

1800 g of the liquid phase P were introduced into a stirred metal vessel (2 l internal volume, helical stirrer virtually scraping the wall).

The temperature of the cooling liquid (water/glycol mixture) transported in the jacket was reduced at a cooling rate of 1 K/h until the resulting crystals suspension (acrylic acid crystals suspended in residual melt) had a solids content of 18% by weight. Thereafter, a part of the crystal suspension was removed and centrifuged on a laboratory centrifuge in a screen beaker equipped with a polypropylene filter fabric at 2000 revolutions per minute for 180 seconds, and the mother liquor thus remaining was virtually completely removed by centrifuging. Analysis of the remaining crystals and of the mother liquor removed by centrifuging gave the depletion coefficient 3.9 for the propionic acid (the depletion coefficient is the ratio of propionic acid remaining in the mother liquor to propionic acid remaining in the crystals, expressed in each case as % by weight based on the total amount of mother liquor or the total amount of crystals).

U.S. Provisional Patent Application No. 60/945393, filed on Jun. 21, 2007, is included in the present Application through literature reference. In view of the abovementioned teachings, numerous amendments and deviations from the present invention are possible. It may therefore be assumed that, within the scope of the attached claims, the invention can be carried out otherwise than specifically described herein.

We claim:

1. A method for the heterogeneously catalyzed partial direct oxidation of n-propane to acrylic acid wherein the n-propane is present in a reaction gas inlet mixture comprising from 100 molppb to 1 mol% of cyclopropane, based on the molar amount of n-propane present in the reaction gas inlet mixture, said method comprising:

feeding to a reaction stage the reaction gas inlet mixture which further comprises molecular oxygen and at least one inert diluent gas, directly partially oxidizing the n-propane present in the reaction gas inlet mixture to acrylic acid in the reaction stage by passing the reaction gas inlet mixture at elevated temperature through a catalyst bed comprising an oxidizing catalyst present in the solid state of aggregation, the conversion of n-propane during a single pass through the catalyst bed being $\geq 10$ mol % and the selectivity of the acrylic acid formation, based on converted n-propane, being $\geq 40$ mol %, feeding the reaction gas mixture, as product gas mixture comprising acrylic acid, out of the reaction stage into a first separation zone, wherein acrylic acid present in the product gas mixture of the reaction stage is converted into the liquid phase in the first separation zone and remaining gaseous residual product gas mixture comprising n-propane and depleted in acrylic acid is removed from the first separation zone and wherein at least a portion of the n-propane present in the residual product gas mixture is recycled to the reaction stage and acrylic acid is separated from the liquid phase in a second separation zone by using at least one thermal separation method, wherein the reaction gas inlet mixture comprises, based on its total volume, from 2 to 50% by volume of n-propane,
from 0.1 to 60% by volume of $CO_2$,
from 1 to 50% by volume of $O_2$,
from 1 to 50% by volume of $H_2O$ and,
from 100 molppb to 1 mol % of cyclopropane, based on the molar amount of n-propane present in the reaction gas inlet mixture; and the at least one thermal separation method in the second separation zone comprises at least one isolation of acrylic acid by crystallization.

2. The method according to claim 1, wherein the oxidizing catalyst is a multimetal oxide.

3. The method according to claim 1, wherein the catalyst is represented by formula (0):

$$J_j M_m N_n Y_y Z_z O_o \quad (0),$$

wherein
J = Mo and/or W;
M = V and/or Ce;
N = Te, Sb and/or Se;
Y = at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu;
Z = Ni, Pd, Cu, Ag and/or Au;
j = 1;
m = from 0.01 to 1;
n = from 0.01 to 1;
y = from 0.01 to 1;
z = from 0.001 to 1; and
o = a number which is determined by the valency and frequency of the elements other than oxygen in (0).

4. The method according to claim 1, wherein the catalyst is represented by formula (I):

$$Mo_1 V_b M^1_c M^2_d \quad (I)$$

wherein
$M^1$ = Te and/or Sb;
$M^2$ = at least one element selected from the group consisting of Nb, Ta, W, Ti, Al, Zr, Cs, Ca, Sr, Ba, Cr, Mn, Ga, Fe, Ru, Co, Rh, Ni, Pd, Pt, La, Bi, Pb, Cu, Re, Ir, V, Pr, Nd, Tb, Ce, Sn, Zn, Si, Na, Li, K, Mg, Ag, Au and In;
b = from 0.01 to 1;
c = from >0 to 1; and
d = from >0 to 1.

5. The method according to claim 1, wherein the catalyst is represented by formula (II):

$$Mo_1 V_b M^1_c M^2_d O_n \quad (II),$$

wherein
$M^1$ = Te and/or Sb;
$M^2$ = at least one element selected from the group consisting of Nb, Ta, W, Ti, Al, Zr, Cs, Ca, Sr, Ba, Cr, Mn, Ga, Fe, Ru, Co, Rh, Ni, Pd, Pt, La, Bi, Pb, Cu, Re, Ir, V, Pr, Nd, Tb, Ce, Sn, Zn, Si, Na, Li, K, Mg, Ag, Au and In;
b = from 0.01 to 1;
c = from >0 to 1;
d = from >0 to 1; and
n = a number which is determined by the valency and frequency of the elements other than oxygen in (II).

6. The method according to claim 1, wherein the catalyst is represented by formula (III):

$$Mo_1 V_{a'} M^4_{b'} M^5_{c'} M^6_{d'} \quad (III),$$

wherein
$M^4$ = at least one element selected from the group consisting of Te and Sb;
$M^5$ = at least one element selected from the group consisting of Nb, Ti, W, Ta and Ce;
$M^6$ = at least one element selected from the group consisting of Pb, Ni, Co, Bi, Pd, Cs, Ca, Sr, Ba, Ag, Pt, Cu, Au, Ga, Zn, Sn, In, Re, Ir, Sm, Sc, Y, Pr, Nd and Tb;
a' = from 0.01 to 1;
b' = from >0 to 1;
c' = from >0 to 1; and
d' = from 0 to 0.5.

7. The method according to claim 1, wherein the catalyst is represented by formula (IV):

$$MO_1 V_{a'} M^4_{b'} M^5_{c'} M^6_{d'} O_{n'} \quad (IV),$$

wherein
$M^4$ = at least one element selected from the group consisting of Te and Sb;
$M^5$ = at least one element selected from the group consisting of Nb, Ti, W, Ta and Ce;
$M^6$ = at least one element selected from the group consisting of Pb, Ni, Co, Bi, Pd, Cs, Ca, Sr, Ba, Ag, Pt, Cu, Au, Ga, Zn, Sn, In, Re, Ir, Sm, Sc, Y, Pr, Nd and Tb;
a' = from 0.01 to 1;
b' = from >0 to 1;
c' = from >0 to 1;
d' = from 0 to 0.5; and
n' = a number which is determined by the valency and frequency of the elements other than oxygen in (IV).

* * * * *